(12) United States Patent
Ferrari

(10) Patent No.: US 9,733,011 B2
(45) Date of Patent: Aug. 15, 2017

(54) FURNITURE CABINET FOR A BREAST PUMP

(71) Applicant: Carlina L. Ferrari, Rockville Centre, NY (US)

(72) Inventor: Carlina L. Ferrari, Rockville Centre, NY (US)

( * ) Notice: Subject to any disclaimer, the term of this patent is extended or adjusted under 35 U.S.C. 154(b) by 0 days.

(21) Appl. No.: 14/858,713

(22) Filed: Sep. 18, 2015

(65) Prior Publication Data
US 2016/0100888 A1    Apr. 14, 2016

Related U.S. Application Data

(60) Provisional application No. 62/071,884, filed on Oct. 6, 2014.

(51) Int. Cl.
| | |
|---|---|
| *A47B 81/00* | (2006.01) |
| *F25D 23/00* | (2006.01) |
| *A61M 1/06* | (2006.01) |
| *F25D 23/12* | (2006.01) |
| *A47B 71/00* | (2006.01) |
| *F25D 25/02* | (2006.01) |

(52) U.S. Cl.
CPC .............. *F25D 23/00* (2013.01); *A47B 81/00* (2013.01); *A61M 1/062* (2014.02); *F25D 23/12* (2013.01); *A47B 71/00* (2013.01); *A61M 2209/06* (2013.01); *A61M 2209/08* (2013.01); *F25D 25/025* (2013.01)

(58) Field of Classification Search
CPC .......... A61M 1/062; F25D 23/00; F25D 3/00; F25D 3/06; F25D 3/08; F25D 2400/12; F25D 2400/20; A47B 81/00; A47B 67/00; A47B 67/02; A47B 71/00
See application file for complete search history.

(56) References Cited

U.S. PATENT DOCUMENTS

| | | | | | |
|---|---|---|---|---|---|
| 2,554,362 | A | * | 5/1951 | Ferguson | A47B 67/02 312/310 |
| 5,399,007 | A | * | 3/1995 | Marconet | A61G 15/14 312/209 |
| 7,665,811 | B2 | * | 2/2010 | Johanning | A61G 12/001 312/209 |
| 7,673,952 | B2 | * | 3/2010 | Jeansonne | A47B 67/04 312/209 |
| 9,161,621 | B1 | * | 10/2015 | Huffin | A47B 81/00 |
| 2011/0109211 | A1 | * | 5/2011 | Kirkeby | A47B 81/00 312/223.6 |
| 2011/0110075 | A1 | * | 5/2011 | Smith | A47B 67/04 362/127 |
| 2011/0115356 | A1 | * | 5/2011 | Nash | A47B 96/021 312/408 |

(Continued)

*Primary Examiner* — Daniel Rohrhoff
(74) *Attorney, Agent, or Firm* — Steven M. Crosby; Feldman Law Group, P.C.

(57) ABSTRACT

The disclosed technology relates to a furniture cabinet capable of storing a breast pump. The furniture cabinet can include a storage section having a door and a slidable platform. The storage section can further include mounts located on an interior of the door. In use, the slidable platform is capable of holding a breast pump motor and the mounts are capable of holding a horn of the breast pump in a standby position when the door is in a closed position.

9 Claims, 12 Drawing Sheets

(56) References Cited

U.S. PATENT DOCUMENTS

| | | | | |
|---|---|---|---|---|
| 2011/0271691 A1* | 11/2011 | Tuszkiewicz | ......... | A47F 3/0408 |
| | | | | 62/3.62 |
| 2013/0327064 A1* | 12/2013 | Stein | ...................... | A47B 37/00 |
| | | | | 62/3.6 |
| 2013/0340467 A1* | 12/2013 | Kiedaisch | .................. | F25D 3/00 |
| | | | | 62/457.2 |
| 2014/0054299 A1* | 2/2014 | Kamin | .................... | F25D 23/00 |
| | | | | 220/592.2 |
| 2014/0196496 A1* | 7/2014 | Ferguson | .................. | F25D 3/06 |
| | | | | 62/449 |
| 2016/0106209 A1* | 4/2016 | Miller | .................... | A47B 81/00 |
| | | | | 312/209 |

\* cited by examiner

FURNITURE CABINET FOR A BREAST PUMP

CROSS REFERENCE TO RELATED APPLICATIONS

This application is based on U.S. Provisional Pat. App. Ser. No. 62/071,884, filed on Oct. 6, 2014. The provisional patent application identified above is incorporated here by reference in its entirety to provide continuity of disclosure.

BACKGROUND

The subject matter described herein relates to a furniture cabinet for a breast pump.

A breast pump is a mechanical device that extracts milk from the breasts of a lactating woman. Breast pumps may be manual devices powered by hand or foot movements or electrical devices powered by electricity or batteries. There are several types of pump mechanisms. Piston pumps draw a piston through a cylinder to create suction. Piston pumps have characteristics of low speed, high reliability, low noise, and long life. Rotary vane pumps use a cam with retractable vanes to create suction. Fast diaphragm pumps use a diaphragm that is acted on by a lever, with thousands of cycles per minute. They operate at higher speed and are usually noisier. Slow diaphragm pumps use a large diaphragm operated by a can or lever to generate suction with each stroke. Pumps have also been designed that use Venturi effects powered by a faucet or water stream, wall suction in hospitals, or pumps powered by oral suctioning.

The most common pumps are electric hospital grade breast pumps and electric personal use pumps. Hospital grade pumps are larger and intended for multiple users. Personal use pumps are smaller and generally intended for one user. Electric breast pumps are powered by a motor which supplies suction through plastic tubing to a horn that fits over a mother's nipple. This style provides a lot more suction, making pumping significantly faster, and allows pumping of both breasts at the same time. Electric breast pumps are ideal for when a mother will be pumping daily. Electric breast pumps are larger than manual ones, but portable models are available (e.g. in a backpack or shoulder bag) that allow the mother to transport the pump. Some manufacturers have battery packs or built in batteries to allow portable operation of the pumps.

Most breast pumps allow direct collection of pumped breast milk into a container that can be used for storage and feeding. The expressed breast milk may be stored and later fed to a baby by bottle. Expressed milk may be kept at room temperature for up to six hours (at 66-72 degrees Fahrenheit), refrigerated for up to 8 days (at 36-44 degrees Fahrenheit), or frozen for 12 months in a freezer maintained at a temperature of −4 to 4 degrees Fahrenheit.

SUMMARY

The disclosed technology relates to a furniture cabinet for a breast pump. The furniture cabinet houses and stores the breast pump in a standby position for easy use and allows the furniture cabinet to maintain an aesthetically-pleasing look within a home or office setting.

In one implementation, a furniture cabinet can be capable of storing a breast pump comprising: a storage section, the storage section including a door and a slidable platform, the storage section further including mounts located on an interior of the door, the slidable platform capable of holding a breast pump motor and the mounts capable of holding at least one horn of the breast pump in a standby position when the door is in a closed position. In some implementations, the at least one horn can be connected to tubing and a milk storage container.

In another implementation, the furniture cabinet can further comprise: a cooling section being lined to protect the outer surface of the furniture cabinet from adverse effects of cold and damp conditions of the cooling section. In some implementations, the cooling section can be cooled with frozen ice packs. In some implementations, the cooling section is cooled by a refrigeration unit.

In another implementation, the furniture cabinet can further comprise: an accessory storage section capable of storing spare parts and replacement milk storage containers.

The advantage of the disclosed technology is that the furniture cabinet houses and stores the breast pump in a standby position for easy use and allows the furniture cabinet to maintain an aesthetically-pleasing look within a home or office setting.

DETAILED DESCRIPTION

Figure 1:
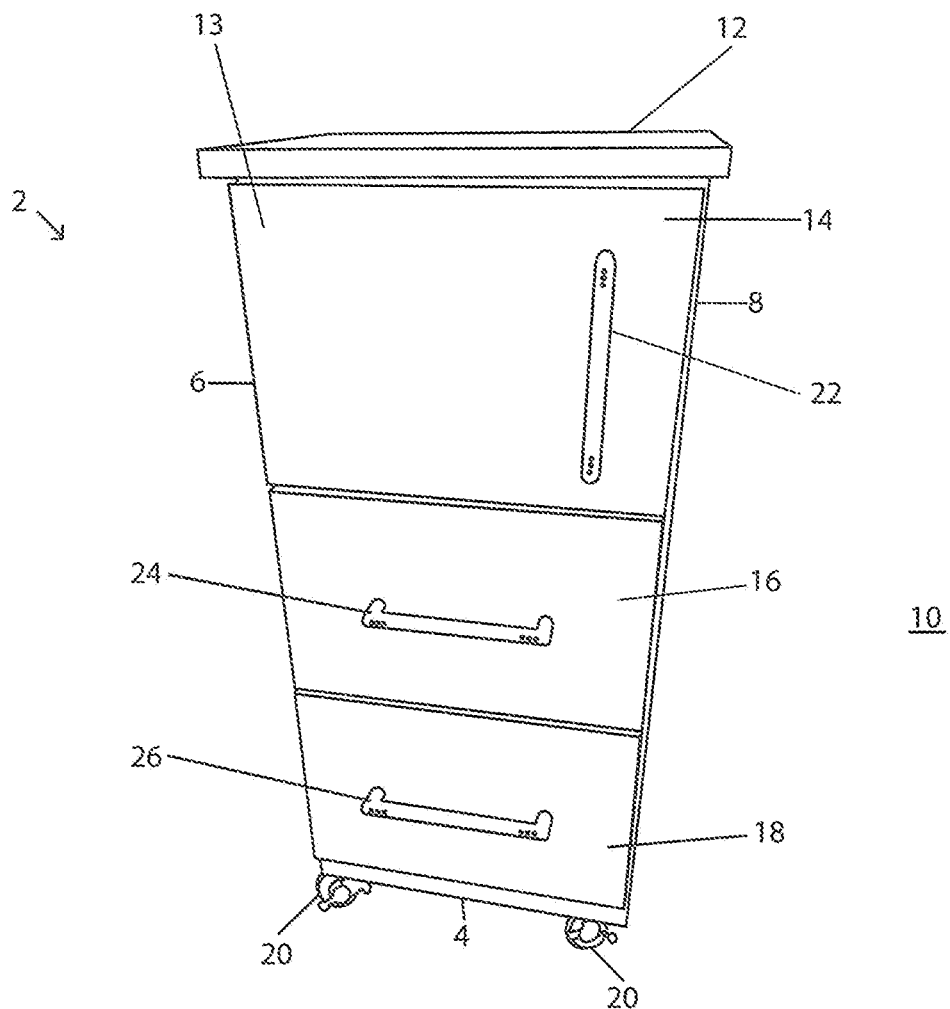
FIG. 1 is a front perspective view of a furniture cabinet of the disclosed technology.
Figure 2:
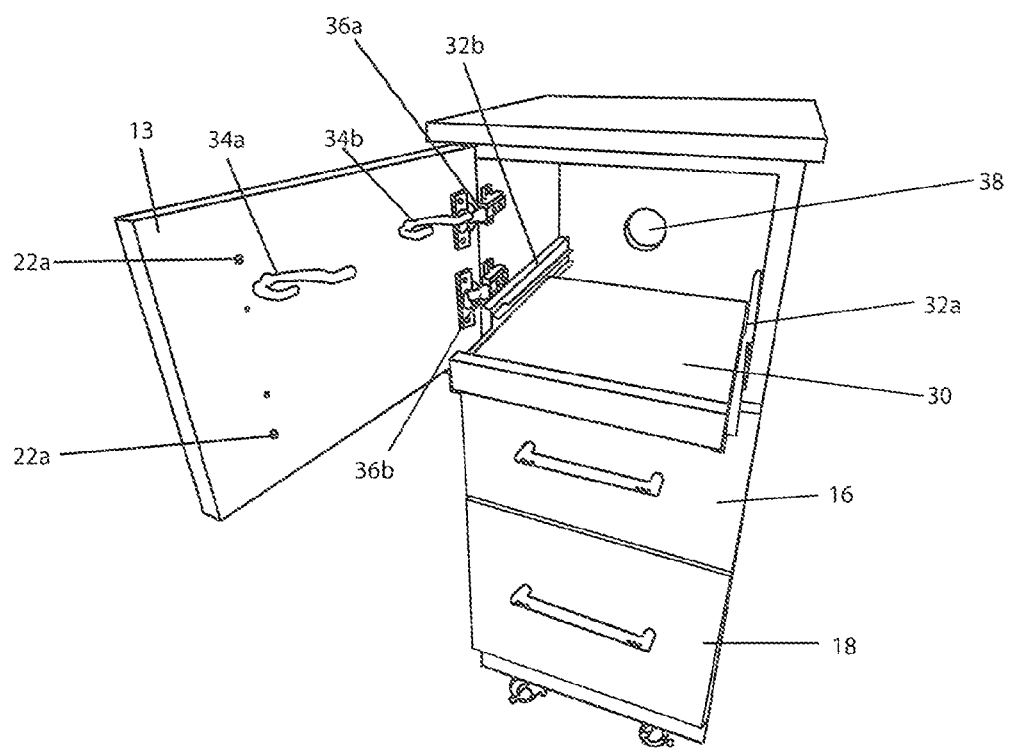
FIG. 2 is a front perspective view of a furniture cabinet of the disclosed technology with an open cabinet door.
Figure 3:
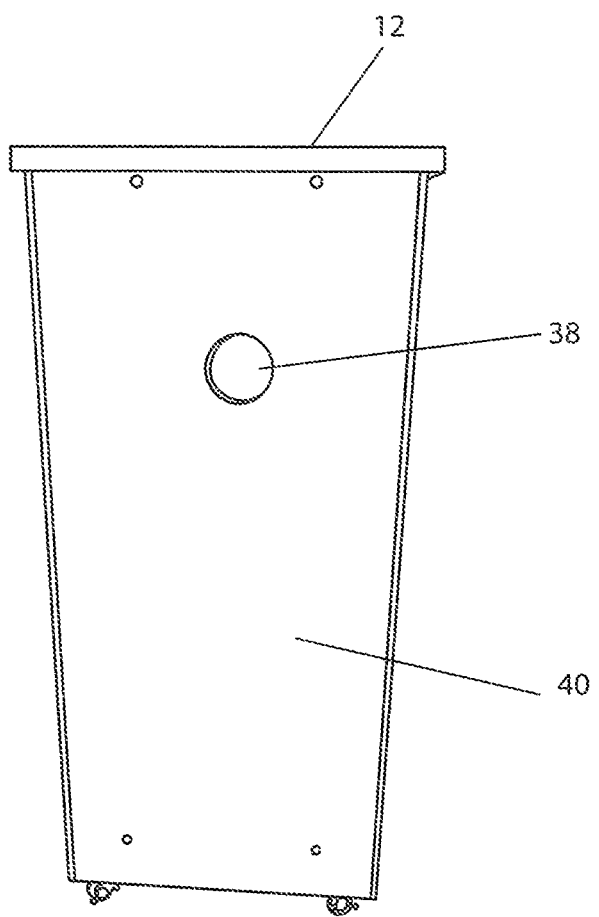
FIG. 3 is a rear view of a furniture cabinet of the disclosed technology.
Figure 4:
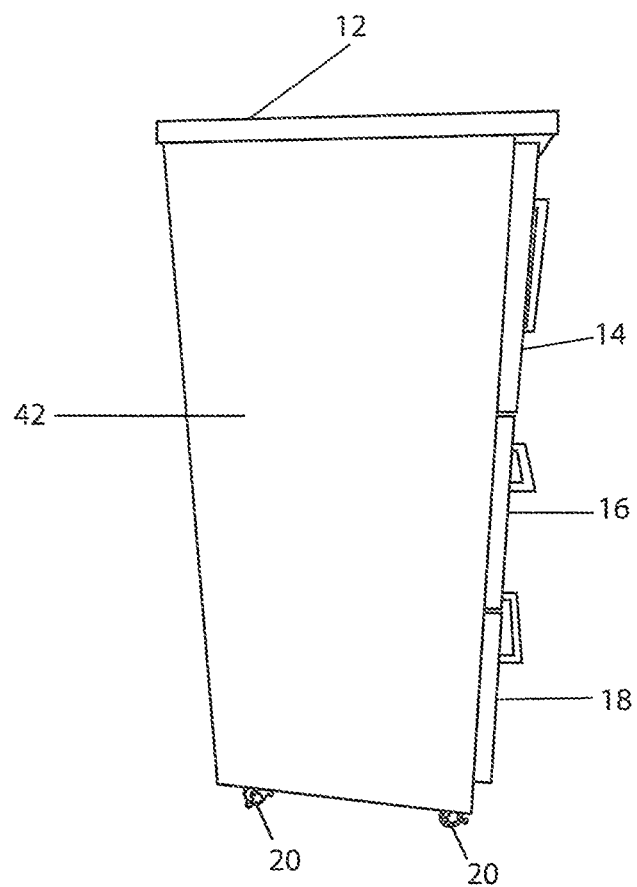
FIG. 4 is a side view of a furniture cabinet of the disclosed technology.
Figure 5:
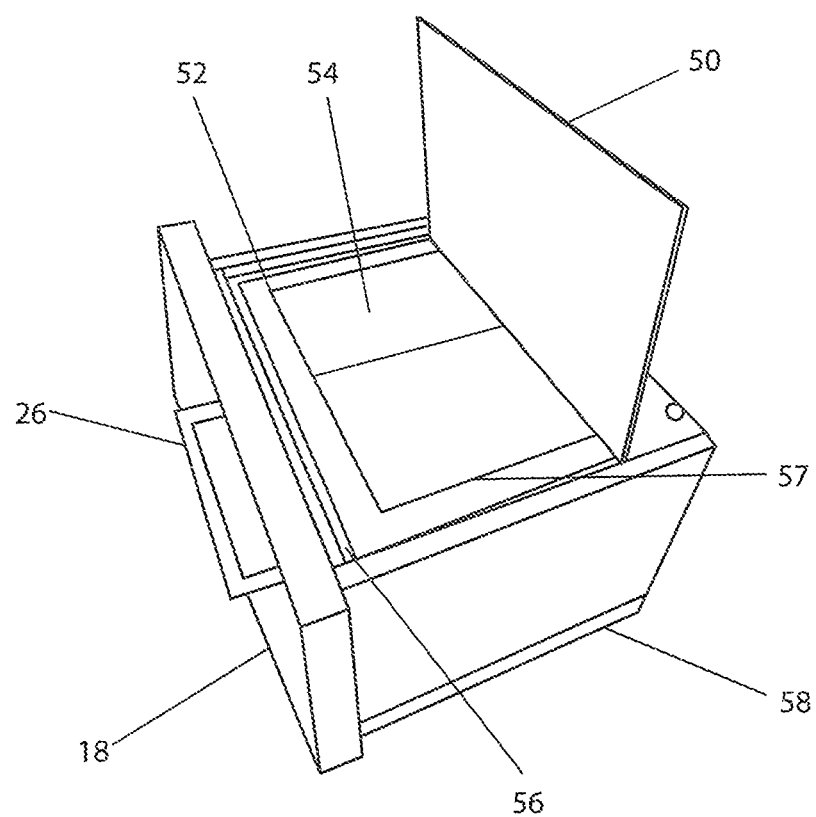
FIG. 5 is a perspective view of an opened cooling drawer of a partial furniture cabinet of the disclosed technology.
Figure 6:
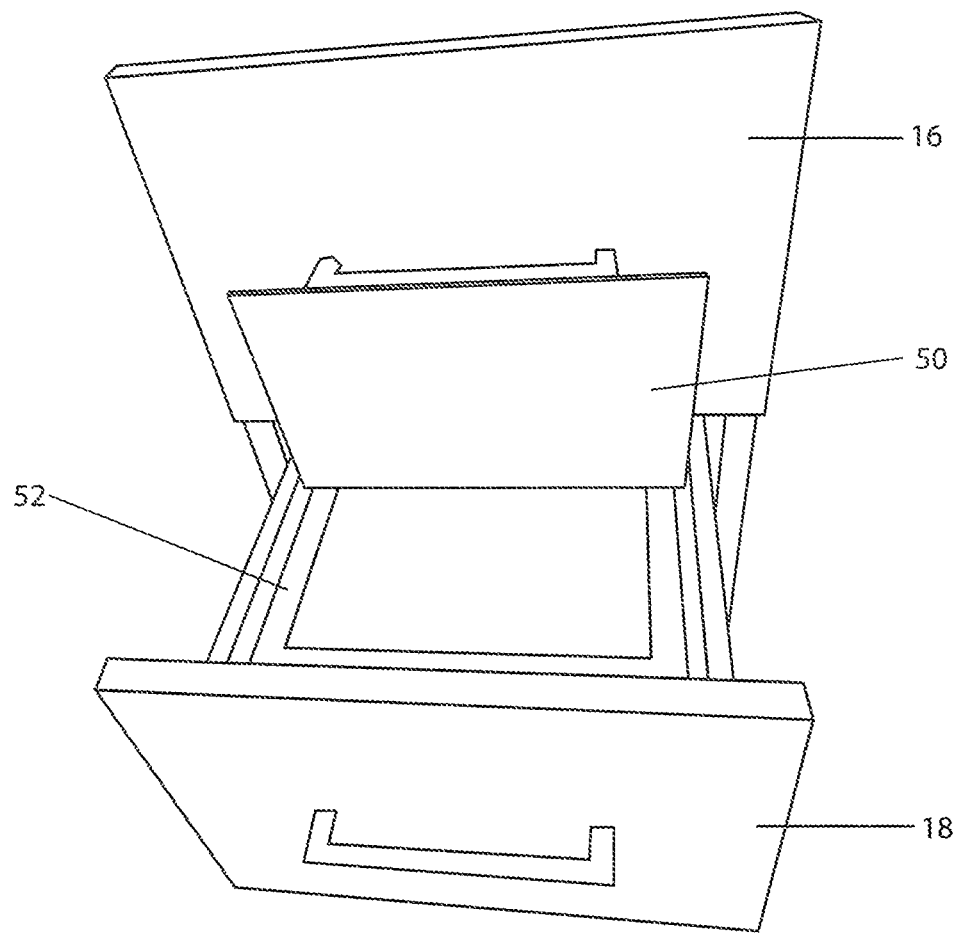
FIG. 6 is a perspective view of an opened cooling drawer of a partial furniture cabinet of the disclosed technology.
Figure 7:
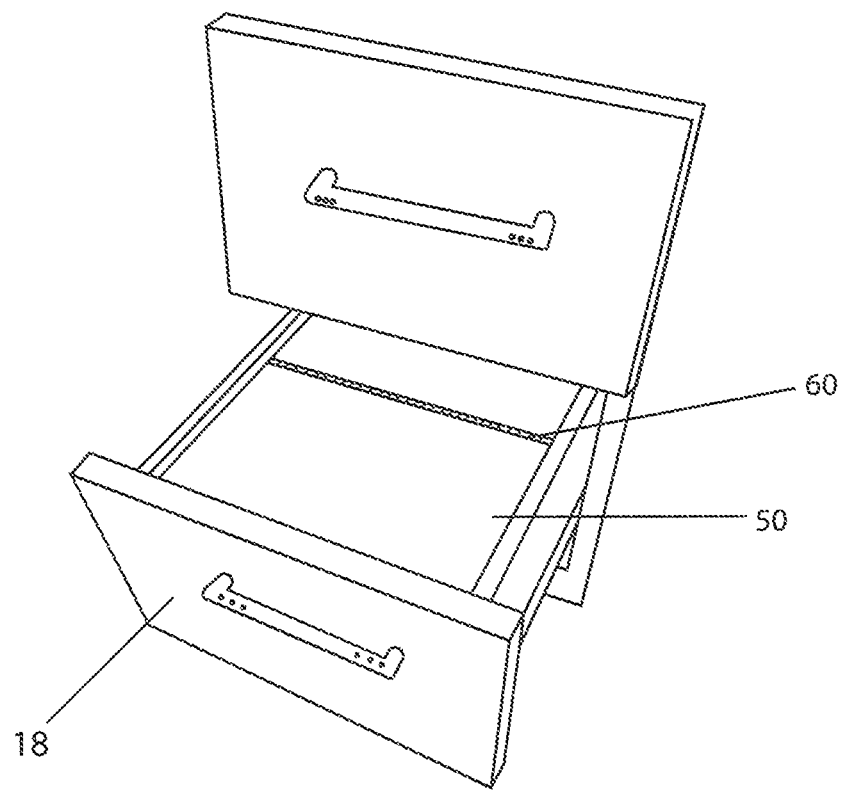
FIG. 7 is a perspective view of a closed cooling drawer of a partial furniture cabinet of the disclosed technology.
Figure 8:
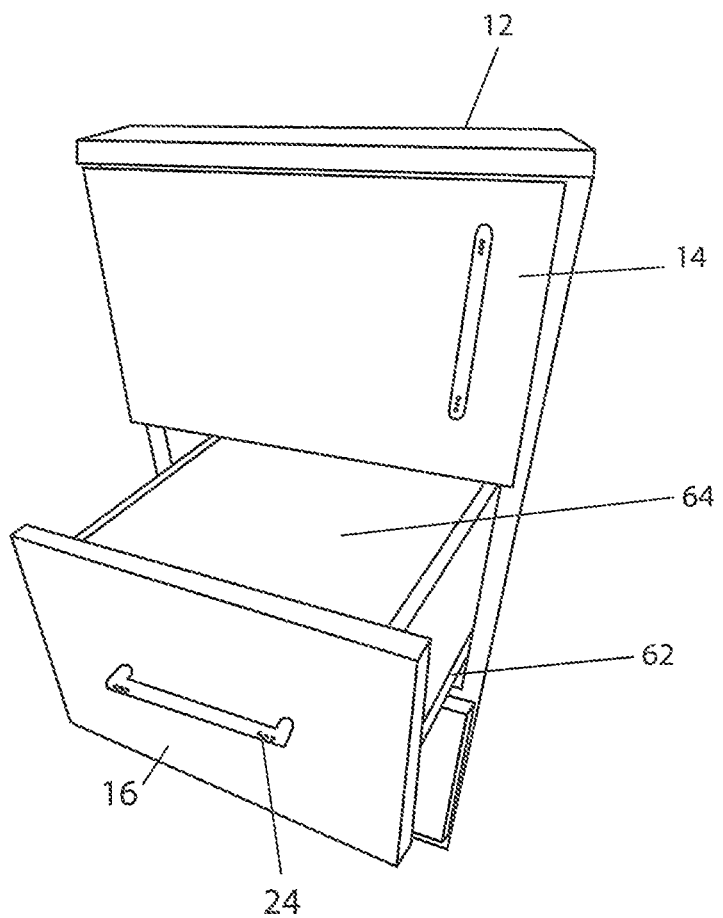
FIG. 8 is a perspective view of an opened storage drawer of a partial furniture cabinet of the disclosed technology.
Figure 9:
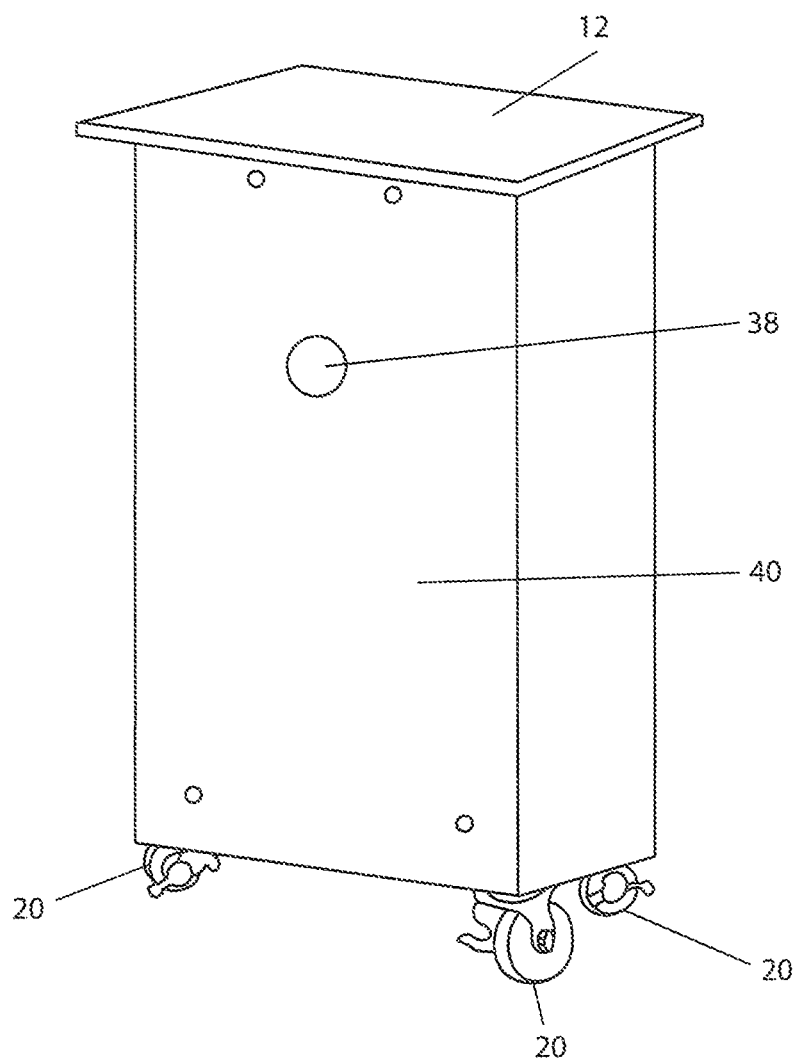
FIG. 9 is a rear perspective view of a furniture cabinet of the disclosed technology.
Figure 10:
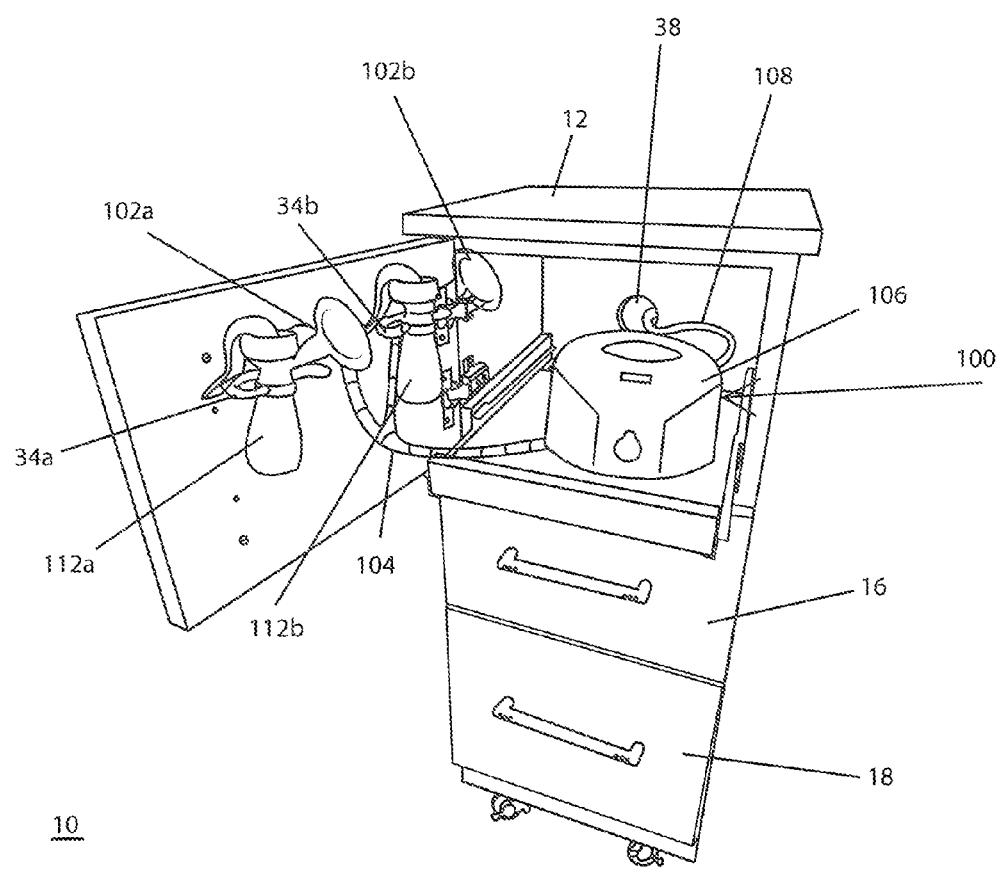
FIG. 10 is a front perspective view of a furniture cabinet of the disclosed technology with an open cabinet door and a breast pump in a standby position.

The disclosed technology relates to a furniture cabinet for a breast pump. The furniture cabinet is capable of housing and storing the breast pump in a standby position for easy use and allows the furniture cabinet to maintain an aesthetically-pleasing look within a home or office setting.

Electric breast pumps are ideal for when a mother will be pumping daily. Electric breast pumps are larger than manual ones, but portable models are available (e.g. in a backpack or shoulder bag) that allow the mother to transport the pump. The problem associated with these portable electric pumps is that each time a mother wants to use the pump there is a certain amount of set up and break down time. Also, the tubing oftentimes gets tangled when in a stored position. Also, if used at home, the motor is usually set up on a piece of furniture or table which is aesthetically unappealing and gives a messy look for any room.

Some electric pumps can be stored in, e.g., a shoulder bag having two positions. The first is the stored position in which a portable pump is packed into the shoulder bag and the second is the working position in which the pump taken out of the shoulder bag and set up in a working position for extracting milk from a breast. A stored standby position is not achievable with a standard shoulder bag. That is, there is always some amount of set up from the stored position to the working position.

As shown in FIGS. 1-10, the disclosed technology overcomes these problems by allowing a breast pump 100 (shown in FIG. 10) to be stored in a standby position within a furniture cabinet 10. While in this position, the horns 102a-b of the breast pump 100 can be placed on mounts 34a-b so that the tubes 104 remain untangled when not in use. The horns can be attached to milk storage containers 112a-b.

In some implementations, the furniture cabinet 10 can be wheeled to different locations throughout a home or office. This allows a mother to have near zero set up time. For example, if sleeping, a mother can easily open the cabinet 10, turn on a motor 106 of the breast pump 100 and start pumping within seconds. Once finished, the milk storage containers 112a-b can be sealed and put in a cooling section 18 of the furniture cabinet 10 at a safe temperature.

FIG. 1 shows a furniture cabinet 10 for specifically housing a breast pump and breast pump supplies needed to support breast pumping mothers while they pump breast milk. The furniture cabinet 10 is convenient, functional, and aesthetically pleasing and fitted with features that allow the tasks of pumping breast milk to be minimized. That is, the furniture cabinet 10 is designed to support mothers while pumping breast milk and, when not in use, to be stored in a standby position in an aesthetically-pleasing storage cabinet.

The furniture cabinet 10 can include a shell 2 having a top panel 12, a bottom panel 4, a left panel 6 and a right panel 8. The dimensions of the furniture cabinet 10 can be, e.g., 29' high, 4" wide and 2' deep but many other sizes are contemplated. The furniture cabinet size is dependent on use, e.g., the furniture cabinet can be shaped as night stand, a file cabinet or any other home or office furniture piece and sized accordingly. The panels 4, 6, 8, 12 of shell 2 can be constructed from finished wood or some other aesthetically-pleasing material.

The shell 2 can also incorporate a top cabinet 14, a middle drawer 16 and a lower drawer 18. The front portions of the top cabinet 16, the middle drawer 14 and the lower drawer 16 can also be constructed from the same material as the panels 4, 6, 8, 12 of the shell 2 giving the furniture cabinet an overall aesthetically-pleasing design.

The top cabinet 14 can house a breast pump 100, e.g., an electric breast pump or any other breast pump known in the art. The top cabinet 14 can include a door 13 attached to the left panel 6 or right panel 8 of the shell with a hinges 36a-b. The hinges 36a-b allow the door 13 to be opened and closed. In some implementations, the opening of the door 13 can cause the breast pump 100 to be put in an on-position.

Within the top cabinet 14, a movable platform 30 can be set on sliding rails 32a-b. The platform 30 allows for easy access to the breast pump 100. The sliding rails 32a-b can be attached to the left and right panel 6, 8 of the shell with mounts. The outside of the door 13 can be equipped with a handle 22 and secured with hardware 22a.

The platform 30 is capable of receiving and retaining a motor portion 106 of the breast pump 100. The platform 30 can be made from a fluid-resistant material so accidental spills will not ruin the integrity of the platform 30. In use, the motor portion 106 can be slide out of the top cabinet 14 so that a user can turn on and off the motor portion 106 as well as change any attachments connected to the motor portion 106. The rear panel 40 of the shell can include an opening 38 for receiving an electric cord 108 of the motor portion 106. That is, the cord 108 can be run from the motor 106 through the hole 38 to an electrical outlet.

The door 13 of the top cabinet 14 can further include mounts 34a-b on an interior thereof. These mounts 34a-b can be, e.g., U-shaped hooks or any other mount capable of holding the horn 102a-b of the breast pump 100. These mounts 34a-b allow for the horn 102 and milk storage containers 112a-b to be stored in a standby position so that once the top cabinet door 13 is opened, a user merely needs to turn on the motor 106 and lift the horn 102 and milk storage containers 112a-b from their standby position into a working position on a breast.

The middle drawer 16 is designed for storage of breast pump components and provisions, e.g., containers, tubing, napkins, etc. The middle drawer 16 can be inserted within the shell 2 using rails 62. The outside of the middle drawer can be equipped with a handle 24 that doubles as a towel bar to hang items such as towels, burp cloths or bibs.

Figure 11:
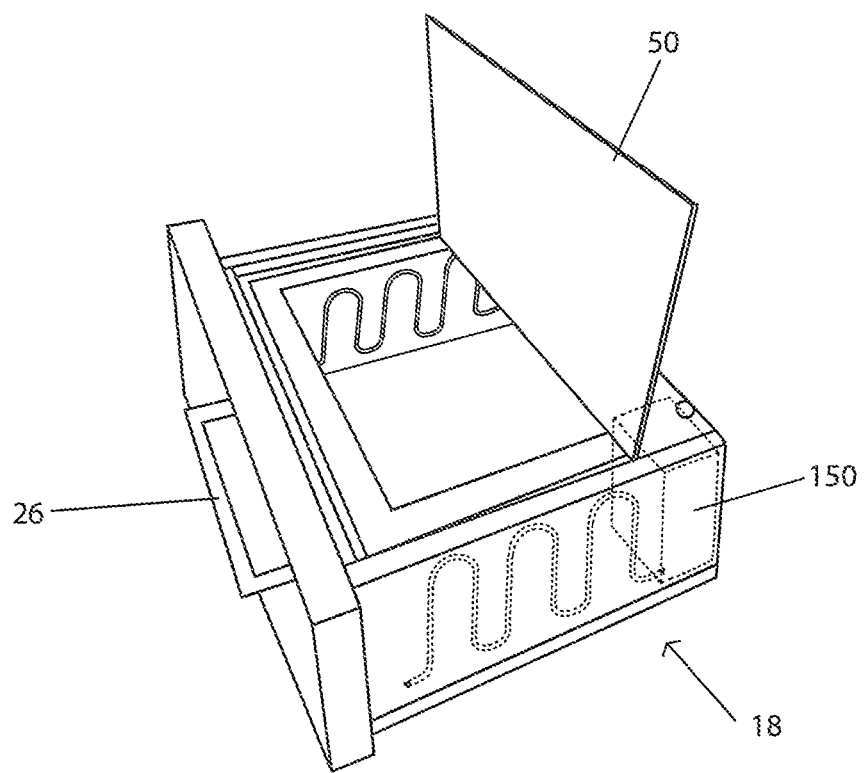
FIG. 11 is a perspective view of an opened cooling drawer having a refrigeration unit.
Figure 12:
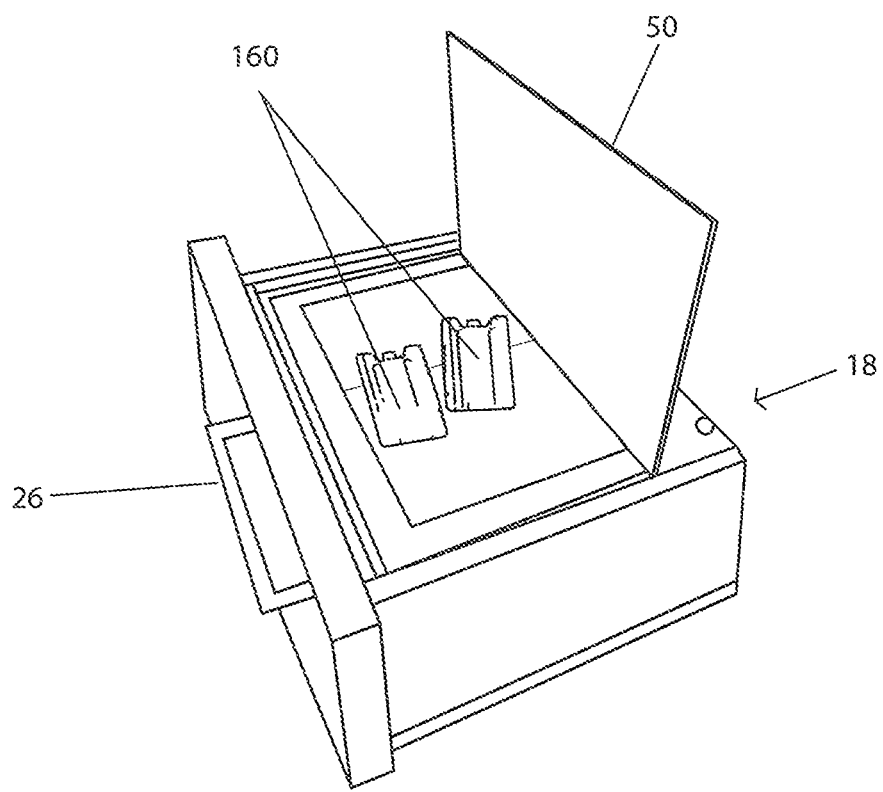
FIG. 12 is a perspective view of an opened cooling drawer having ice packs.

The lower drawer 18 of the furniture cabinet 10 can be insulated allowing for cool storage of pumped breast milk. The lower drawer 18 can be inserted within the shell 2 using rails 58. The lower drawer 18 can include a cooler 54 with a hinged top door 50, a first insulating layer 56 and a second insulating layer 57. In some implementations, the door of the cooler can be a sliding door, can be incorporated into the furniture cabinet itself or can be any door for maintaining the temperature within the cooler. For example, as shown in FIG. 12, the first insulating layer 56 retains a cool state of an ice pack 160 for allowing stored breast milk to remain cool. The second insulting layer 57 allows for protecting the shell 2 of the cabinet 10 from damage by condensation or leaking breast milk containers from the cooler 54. In some implementations, the lower drawer 18 can be insulated with foam insulation board and sheet aluminum for cool storage of breast milk and cold packs. The outside of the lower drawer can be equipped with a handle 26 that doubles as a towel bar to hang items such as towels, burp cloths or bibs. In some implementations, as shown in FIG. 11, the lower drawer 18 can include a powered refrigeration or freezer unit 150.

Please note, the configuration of the cabinets and drawers can also be interchanged based on the type and size of the furniture piece the furniture cabinet is meant to resemble.

The furniture cabinet 10 can be mobile, e.g., the furniture cabinet can be equipped with four wheels or casters 20, which allows breast pumping mothers an opportunity to change pumping locations with ease. In some implementations, the wheels or casters 20 can be hidden from view by a skirt.

The foregoing Detailed Description is to be understood as being in every respect illustrative and exemplary, but not restrictive, and the scope of the disclosed technology disclosed herein is not to be determined from the Detailed Description, but rather from the claims as interpreted according to the full breadth permitted by the patent laws. It is to be understood that the embodiments shown and described herein are only illustrative of the principles of the disclosed technology and that various modifications may be implemented by those skilled in the art without departing from the scope and spirit of the disclosed technology. Those skilled in the art could implement various other feature combinations without departing from the scope and spirit of the disclosed technology. Although the embodiments of the present disclosure have been described with specific examples, it is to be understood that the disclosure is not limited to those specific examples and that various other changes, combinations and modifications will be apparent to one of ordinary skill in the art without departing from the scope and spirit of the disclosed technology which is to be determined with reference to the following claims.

The invention claimed is:

1. A furniture cabinet capable of storing a breast pump comprising:
   a breast pump, the breast pump including a motor, horns and tubing, the motor being connected to the horns via the tubing; and
   a storage section, the storage section including a door and a slidable platform, the storage section further including mounts located on an interior of the door, the slidable platform holding the breast pump motor and the mounts holding at least one horn of the breast pump in a standby position when the door is in a closed position.

2. The furniture cabinet of claim 1 further comprising:
   a cooling section being lined to protect the outer surface of the furniture cabinet from adverse effects of cold and damp conditions of the cooling section.

3. The furniture cabinet of claim 2 wherein the cooling section is cooled with frozen ice packs.

4. The furniture cabinet of claim 2 wherein the cooling, section is cooled by a refrigeration unit.

5. The furniture cabinet of claim 1 further comprising:
   an accessory storage section capable of storing spare parts and replacement milk holders.

6. The furniture cabinet of claim 1 wherein the at least one horn is attached to a milk storage container.

7. A furniture cabinet capable of storing a breast pump comprising:
   a shell, the shell being constructed from wood;
   a storage section, the storage section being incorporated into the shell, the storage section including a door and a slidable platform, the storage section further including mounts located on an interior of the door, the slidable platform capable of holding a breast pump motor and the mounts capable of holding at least one horn of the breast pump so that tubes connecting the breast pump motor to the at least one horn can remain untangled in a standby position when the door of the furniture cabinet is in a closed position; and
   a cooling section, the cooling section being incorporated into the shell, the cooling section including a first insulating layer and a second insulating layer, wherein the first insulating layer retains a cool state within the cooling section and the second insulting layer protects the wood of the shell from damage due to condensation.

8. A furniture cabinet capable of storing a breast pump comprising:
   a storage section, the storage section including a door and a slidable platform, the storage section further including mounts located on an interior of the door, the slidable platform capable of holding a breast pump motor and the mounts capable of holding at least one horn of the breast pump in a standby position when the door is in a closed position, the slidable platform being made from a fluid-resistant material in order to protect the platform from damage by fluid.

9. The furniture cabinet of claim 8 further comprising:
   a cooling section, the cooling section including a first insulating layer and a second insulating layer, wherein the first insulating layer retains a cool state within the cooling section and the second insulting layer protects a shell of the furniture cabinet from damage due to condensation.

* * * * *